(12) United States Patent
Sasaki et al.

(10) Patent No.: US 7,885,376 B2
(45) Date of Patent: Feb. 8, 2011

(54) X-RAY CT APPARATUS

(75) Inventors: Tomiya Sasaki, Nasushiobara (JP);
Yohei Matsuzawa, Nasushiobara (JP)

(73) Assignees: Kabushiki Kaisha Toshiba, Tokyo (JP);
Toshiba Medical Systems Corporation, Otawara-Shi ( * ) Notice: Subject to any disclaimer, the term of this patent is extended or adjusted under 35 U.S.C. 154(b) by 0 days.

(21) Appl. No.: 11/319,704

(22) Filed: Dec. 29, 2005

(65) Prior Publication Data

US 2006/0165212 A1 Jul. 27, 2006

(30) Foreign Application Priority Data

Jan. 5, 2005 (JP) ............................. 2005-000787

(51) Int. Cl.
*G01N 23/00* (2006.01)
(52) U.S. Cl. ......................................... 378/15; 378/197
(58) Field of Classification Search ............... 378/4–20, 378/193, 196, 197
See application file for complete search history.

(56) References Cited

U.S. PATENT DOCUMENTS

| 4,115,695 | A | * | 9/1978 | Kelman ....................... 378/17 |
| 5,982,844 | A | * | 11/1999 | Tybinkowski et al. .......... 378/4 |
| 2002/0015470 | A1 | * | 2/2002 | Tybinkowski et al. ......... 378/17 |
| 2004/0179644 | A1 | * | 9/2004 | Tsuyuki ........................ 378/8 |
| 2005/0226385 | A1 | * | 10/2005 | Simpson et al. ............. 378/132 |

FOREIGN PATENT DOCUMENTS

JP 2003-93379 4/2003

* cited by examiner

*Primary Examiner*—Hoon Song
(74) *Attorney, Agent, or Firm*—Oblon, Spivak, McClelland, Maier & Neustadt, L.L.P.

(57) ABSTRACT

An X-ray CT apparatus comprises a rotating part, a fixed frame and a stand. The rotating part mounts an X-ray tube and a detector. The fixed frame supports the rotating part. The stand settled to a floor supports the fixed frame. The stand includes a lower member, supporters and a fixing member. The lower member is settled to the floor. Each of the supporters settled to the lower member supports each side of the fixed frame. The fixing member fixes a lower part of the fixed frame with the lower member.

15 Claims, 8 Drawing Sheets

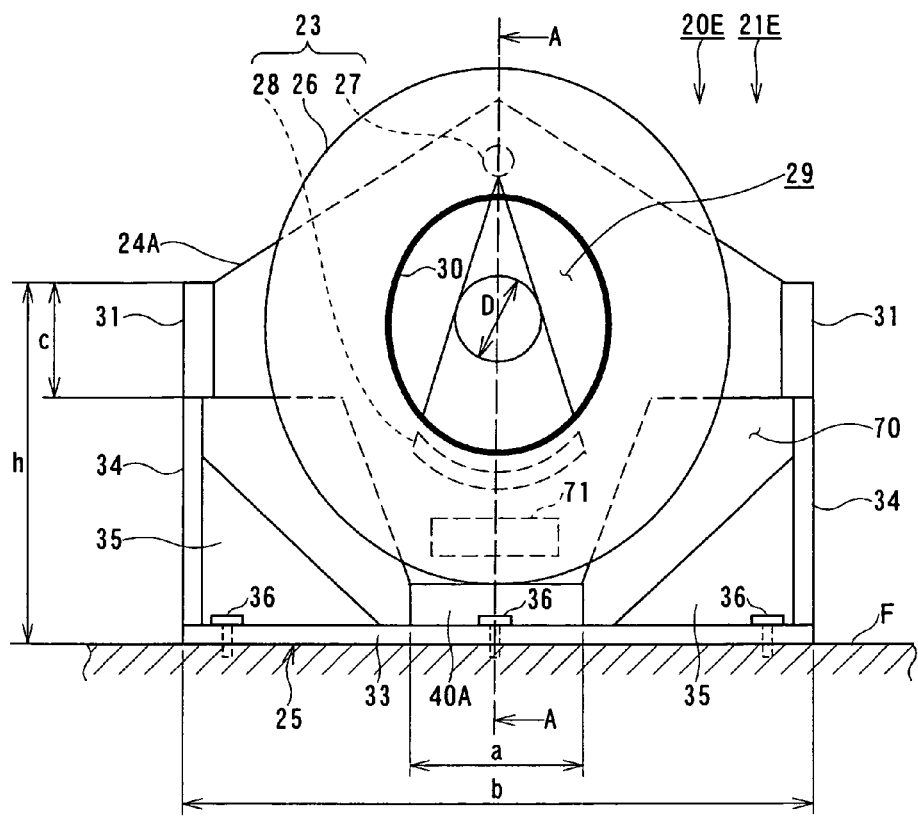
F I G. 12
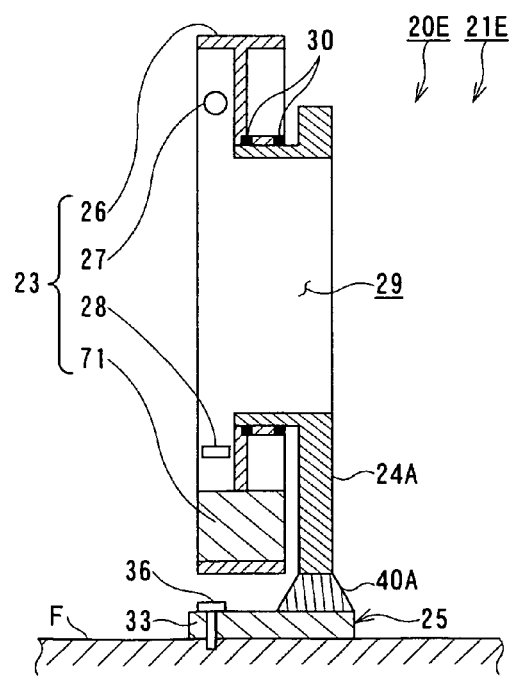
F I G. 13

X-RAY CT APPARATUS

BACKGROUND OF THE INVENTION

1. Field of the Invention

The present invention relates to an X-ray CT (computed tomography) apparatus including an X-ray CT gantry in which strength and rigidity are improved.

2. Description of the Related Art

X-ray CT apparatuses have become widespread as apparatuses for medical diagnosis (see, for example, Japanese Patent Application (Laid-Open) No. 2000-116644). X-ray CT apparatuses include a gantry incorporating an X-ray tube, a detector, a power supply, and components for processing a signal. An imaging opening for imaging an object is formed in the central portion of the gantry of the X-ray CT apparatus. Components including the X-ray tube and the detector are contained in a box-like container member, which is a part of the gantry, and are arranged on either side of the imaging opening.

In a helical scan X-ray CT apparatus, components including an X-ray tube and a detector rotate about an object to be imaged, and therefore, the components including the X-ray tube and the detector form a rotating unit. The whole body of the X-ray CT apparatus is surrounded by a cover to protect the inside of the X-ray CT apparatus.

FIG. 14 is a front view showing a structure of a conventional X-ray CT apparatus. FIG. 15 is a side view of the conventional X-ray CT apparatus shown in FIG. 14.

An X-ray CT apparatus 1 includes a gantry 2. The gantry 2 is surrounded by a cover (not shown). The gantry 2 includes a rotating part 3, a mainframe 4, and a stand 5. The rotating part 3 includes a donut-shaped rotating base 3a, which incorporates an X-ray tube, a high-voltage generation unit, a detector, a board for controlling X-rays and other components, and electric components, e.g., power supply (each not shown). The interior of the rotating part 3 serves as an imaging area S. Additionally, the rotating base 3a of the rotating part 3 is mounted on the planar mainframe 4 with a bearing 6 therebetween. A shaft-like supporting unit 7 is provided on either side of the mainframe 4. The axis direction of the supporting unit 7 is horizontal and substantially perpendicular to a rotation axis of the rotating part 3.

On the other hand, the stand 5 includes supporters 8 each perpendicular to the mounting surface of the X-ray CT apparatus 1, an extendable rod-like actuator 9, and electric components 10 contained in a metallic box. The supporting unit 7 mounted on either side of the mainframe 4 is supported by the supporter 8 of the stand 5 in a rotatable manner about the axis of the supporting unit 7. Furthermore, the other part of the mainframe 4 is supported by the actuator 9.

Accordingly, the rotating part 3 and the mainframe 4 are tiltable about the axis of the supporting unit 7 so that a two-dimensional image data of an object can be obtained at a desired angle.

Additionally, an X-ray CT apparatus has been proposed in which a LM (Linear Motion) guide is provided on either side of a stand to maintain the supporting rigidity of a gantry (see, for example, Japanese Patent Application (Laid-Open) No. H6-178769).

However, in a known X-ray CT apparatus having a tiltable gantry, a backlash occurs between a tilt structure and a supporting unit and between a stand and the supporting unit. Therefore, when obtaining a high-resolution image in an area in all the radial directions of a rotating part, the error corresponding to the backlash has an adverse effect on the image, which is a problem. It is known that, as the inner diameter of the rotating part (i.e., the imaging area) increases, the effect of the backlash on the image becomes more significant. In addition, recently, the imaging area in a radial direction of an X-ray CT apparatus has become larger. As a result, to reduce the error caused by the backlash, a damper is provided at a variety of locations of the X-ray CT apparatus. Also, a special positioning process is performed. That is, extra components or extra man-hours are required to reduce the error.

Furthermore, in recent X-ray CT apparatuses, a gantry including a rotating part rotating at high speeds is generally used. Accordingly, even a slight imbalance may cause a large force, and therefore, adjustment of the balance is critical. However, it is difficult to completely eliminate the imbalance, and therefore, a stand serving as a base is required to be reinforced as well as the whole gantry.

Still furthermore, in recent X-ray CT apparatuses, a two-dimensional detector having detecting elements of which each size is about 0.5 mm by 0.5 mm is generally used. Accordingly, various factors including a backlash in a tilt structure cause vibration of the gantry. The vibration of the gantry has a serious impact on the image quality.

In a known X-ray CT apparatus including an LM guide, the strength of a gantry depends on the strength of a stand. Accordingly, even when the rigidity of the LM guide which is provided on either side of the stand is increased, the increase in the rigidity does not directly result in the increase in the rigidity and strength of the gantry. Also, since two costly LM guides are necessary, this solution is not desirable in terms of cost effectiveness.

SUMMARY OF THE INVENTION

The present invention has been made in light of the conventional situations, and it is an object of the present invention to provide an X-ray CT apparatus which makes it possible to give large strength and rigidity to its gantry using a simpler reinforcement without increasing strength of elements including stands and support elements supporting its rotating part beyond necessity.

The present invention provides an X-ray CT apparatus comprising: a rotating part mounting an X-ray tube and a detector; a fixed frame supporting the rotating part; and a stand supporting the fixed frame, the stand being settled to a floor, wherein the stand includes: a lower member settled to the floor; supporters each supporting each side of the fixed frame, the supporters being settled to the lower member; and a fixing member fixing a lower part of the fixed frame to the lower member, in an aspect to achieve the object.

The present invention also provides an X-ray CT apparatus comprising: a rotating part mounting an X-ray tube and a detector; a mainframe supporting the rotating part; a lower member of a stand united with a lower part of the mainframe, the lower member being settled to a floor; and supporters each supporting each side of the mainframe, the supporters being settled to the lower member, in an aspect to achieve the object.

The present invention also provides an X-ray CT apparatus comprising: a rotating part mounting a device for generating an X-ray and a device for detecting the X-ray; a fixed frame supporting the rotating part on contact with a rotary drive structure; and a stand supporting the fixed frame by at least three supporting points, wherein the fixed frame and the stand is configured to form a space for a maintenance of at least one of the device for generating the X-ray and the device for detecting the X-ray between one of the three supporting points and another, in an aspect to achieve the object.

The X-ray CT apparatus as described above make it possible to give large strength and rigidity to its gantry using a simpler reinforcement without increasing strength of elements including stands and support elements supporting its rotating part beyond necessity.

BRIEF DESCRIPTION OF THE DRAWINGS

In the accompanying drawings:

FIG. 12 is a front view showing a gantry of an X-ray CT apparatus according to a fifth embodiment of the present invention;

FIG. 13 is a sectional view on A-A of the gantry shown in FIG. 12.

DESCRIPTION OF THE PREFERRED EMBODIMENTS

An X-ray CT apparatus according to embodiments of the present invention will be described with reference to the accompanying drawings.

Figure 1:
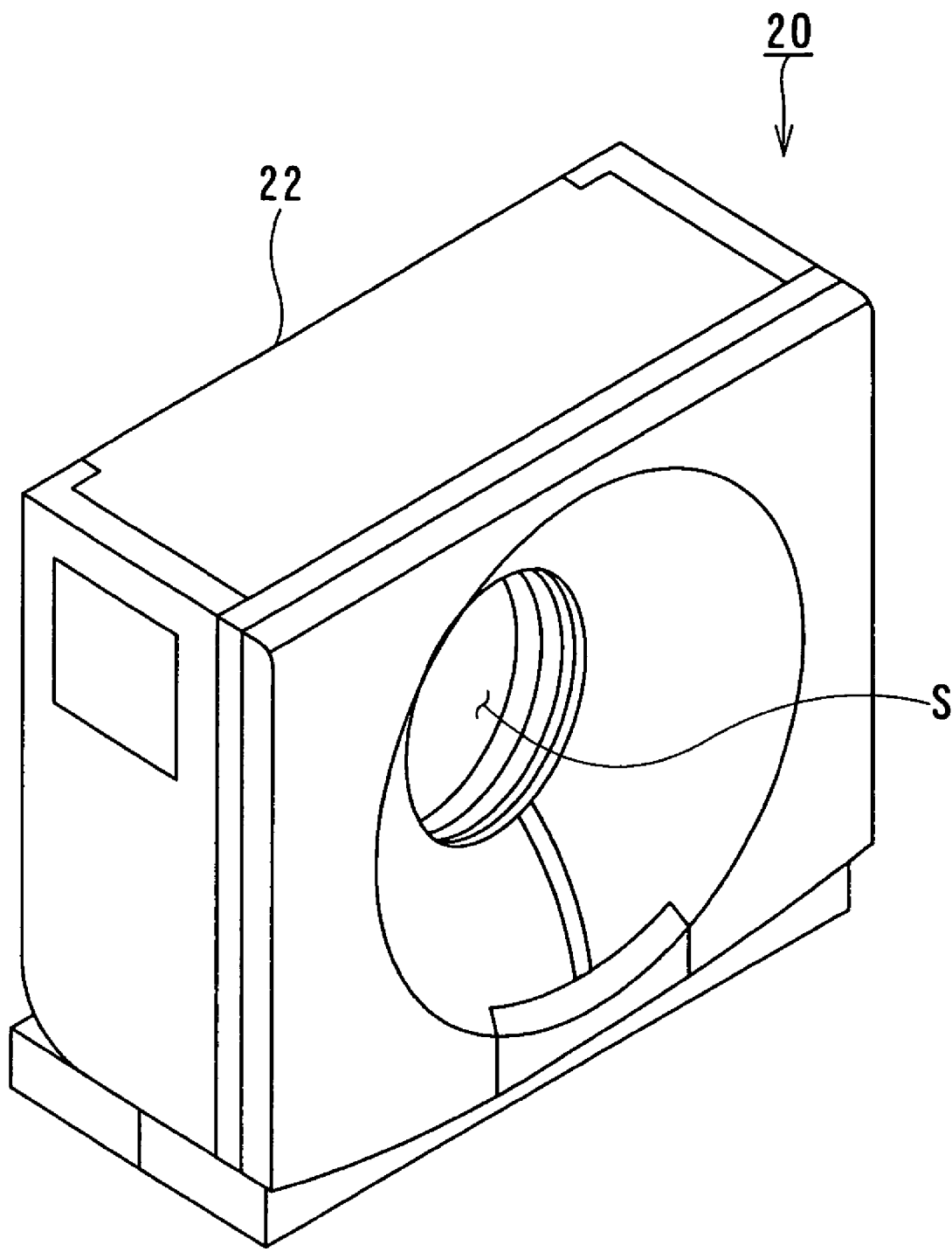
FIG. 1 is a perspective view showing an X-ray CT apparatus according to a first embodiment of the present invention.
Figure 2:
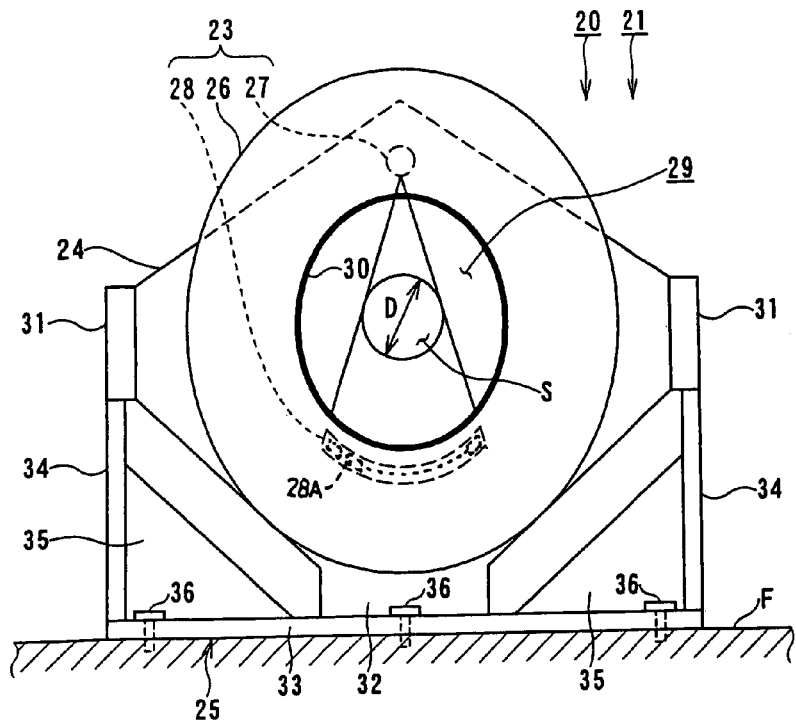
FIG. 2 is a front view showing a structure of the gantry in a state where the cover was removed of the X-ray CT apparatus shown in FIG. 1.
Figure 3:
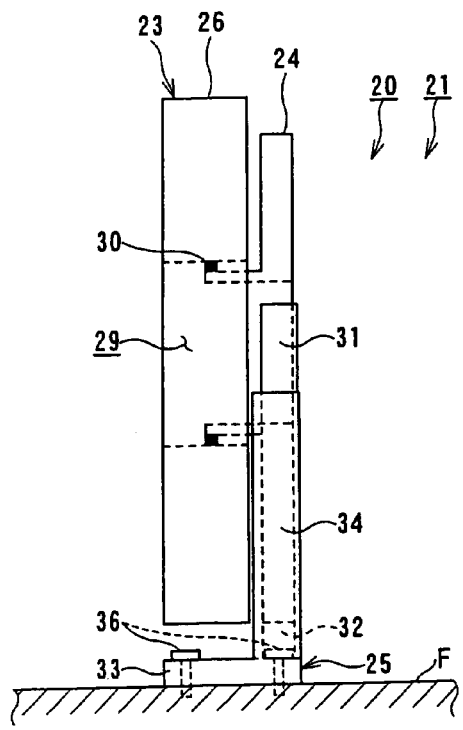
FIG. 3 is a side view of the gantry shown in FIG. 2.

FIG. 1 is a perspective view showing an X-ray CT apparatus according to a first embodiment of the present invention. FIG. 2 is a front view showing a structure of the gantry 21 in a state where the cover 22 was removed of the X-ray CT apparatus 20 shown in FIG. 1. FIG. 3 is a side view of the gantry 21 shown in FIG. 2.

An X-ray CT apparatus 20 includes a gantry 21, which is a main component. The gantry 21 is surrounded by a cover 22. The gantry 21 includes a rotating part 23, a mainframe 24, and a stand 25. The rotating part 23 includes a rotational base 26 having a donut shape with a hollow center. The rotational base 26 incorporates an X-ray tube 27, a detector 28 including a plurality of detecting elements, a high-voltage generation unit (not shown), a board for controlling X rays and other components (not shown), and electric components (e.g., a power supply) (not shown).

An imaging opening 29 for imaging an object is formed at the center of the rotating part 23. An imaging area S having a diameter D is formed between the X-ray tube 27 and the detector 28. Additionally, the rotational base 26 of the rotating part 23 is mounted on the plate-like mainframe 24 with a bearing 30 therebetween. The bearing 30 is an example of a rotary drive structure. As a result, the rotating part 23 can rotate about a rotation axis of the bearing 30 relative to the mainframe 24.

A side supporting part 31 of any shape is provided to either side surface of the mainframe 24. Furthermore, a lower supporting part 32 is formed in a lower section of the mainframe 24, which is closer to the mounting surface of the X-ray CT apparatus 20 than at least the center of gravity of the mainframe 24. The lower supporting part 32 is composed of, for example, a metallic plate. The lower supporting part 32 fixes the mainframe 24 to the stand 25 by means of screwing, welding or other equivalent means.

On the other hand, the stand 25 includes a lower member 33 and supporters 34. Each of the supporters 34 are provided to the lower member 33 substantially perpendicular to the mounting surface of the X-ray CT apparatus 20. Also, electric components 35 contained in a metallic box are provided to the stand 25 as needed. The side supporting part 31 provided to either side of the mainframe 24 is supported by the supporter 34 of the stand 25. Furthermore, the lower supporting part 32 of the mainframe 24 is integrated into the lower member 33 of the stand 25 and is supported by the lower member 33 of the stand 25.

In the structure in which the lower supporting part 32 of the mainframe 24 is supported by the lower member 33 of the stand 25, other members or components may be provided between the lower member 33 of the stand 25 and the lower supporting part 32 of the mainframe 24. Accordingly, the lower supporting part 32, which is a lower section of the mainframe 24 adjacent to the mounting surface, is secured to the stand 25, either directly or indirectly.

Furthermore, the lower member 33 of the stand 25 is settled with a floor F by an arbitrary method for settling. For example, the lower member 33 is settled with the floor F at four portions near the supporters 34 and a portion near the lower supporting part 32 of the mainframe 24 with a total of five anchor bolts 36 respectively. In this manner, fixing the stand 25 with the floor F at portions to which load is applied makes it possible to suppress vibration of the rotating part 23 relative to the gantry 21 to reduce degradation of quality of images even if rotary vibration occurs on imaging. In addition, the gantry 21 can be tightly fixed with the floor F.

In the X-ray CT apparatus 20 having such a structure, the mainframe 24 is supported by the stand 25 at three points, that is, the bottom of the mainframe 24 in addition to the both sides of the mainframe 24 are supported. As a result, a backlash of the gantry 21 is eliminated, which is a problem of the known X-ray CT apparatus 1 having a tilt structure in which the mainframe 24 is supported by the stand 25 at two points. Thus, greater strength and rigidity can be provided to the gantry 21 in a simpler manner.

The impact of a backlash of the gantry 21 on an image is now herein described briefly. If the outermost portion of the imaging area S is displaced by 0.5 mm, a tumor or a bone that is smaller than the size corresponding to the displacement cannot be observed in the corresponding area in a cross-sectional image. Additionally, the displacement of the rotating part 23 tends to cause an artifact or a ring in the image. Consequently, these negative impacts on the image decrease the effect of early diagnosis or spoil a treatment plan.

In contrast, the X-ray CT apparatus 20 can reduce the displacement of the rotating part 23 and the mainframe 24. Accordingly, the quality or performance of an image captured by the X-ray CT apparatus 20 can be significantly increased, and therefore, the reliability of the image can be increased. In addition, according to the X-ray CT apparatus 20, a small part can be observed, thus increasing the effect of the early diagnosis. Also, the treatment plan can be carried out early and appropriately.

Furthermore, since the X-ray CT apparatus 20 does not employ a tilt structure, the manufacturing cost can be reduced and the X-ray CT apparatus 20 can be reinforced by a simple structure. That is, the X-ray CT apparatus 20 can obtain a large strength and rigidity without the need to reinforce the components (e.g., the stand 25) and without the need for an additional support member. The X-ray CT apparatus 20 can sufficiently support a high-speed rotation. In addition, even when the size of the imaging area S is increased in the radial direction, a high-quality image can be obtained. Accordingly, a large and heavy multi-slice X-ray CT apparatus which includes the detector 28 having X-ray detecting elements arranged at a plurality of rows 28A (preferably, 60 rows and above) for acquiring volume data is can be achieved. In particular, when the rotating part 23 rotates at a speed higher than 0.5 seconds per rotation, or when a width of a detecting element of the detector 28 is smaller than or equal to 0.5 mm, or when the slice thickness of an image reconstructed on the basis of the output from the detector 28 is less than 0.5 mm, or when the positional error needs to be less than or equal to 0.5 mm at the periphery of the imaging area S in the X-ray CT apparatus 20 having a diameter D of the imaging area S greater than about 500 mm, or when a space for inserting an object has an opening having a diameter of 900 mm above, advantage of the invention can be obtained.

Additionally, due to the improvement of 3-D image processing technology, even when the tilt structure is removed, any cross-sectional image can be easily reconstructed from slice image data in a single direction. Accordingly, nowadays, the need for high precision imaging technology in accordance with the increase in the diameter of the imaging area S and high-speed rotation of the rotating part 23, which is not required in known X-ray CT apparatuses, is more desirable than the need for providing a tilt structure to the X-ray CT apparatuses. In this regard, the X-ray CT apparatus 20 shown in FIG. 1 meets the need for high-precision imaging technology.

In particular, the recent X-ray CT apparatuses can reduce the thickness of a slice of a cross-sectional image. Accordingly, by reducing a mechanical backlash in all directions, the X-ray CT apparatus 20 can reconstruct and display a clearer image with higher-resolution.

In addition, in a structure in which at least a lower section of the mainframe 24 is secured to the stand 25, the mainframe 24 may be supported by the stand 25 at three points or more, regardless of the upper and lower sections of the mainframe 24. Additionally, a desired portion of the mainframe 24 can be in line contact with or in surface contact with the stand 25 so as to form the gantry 21.

Figure 4:
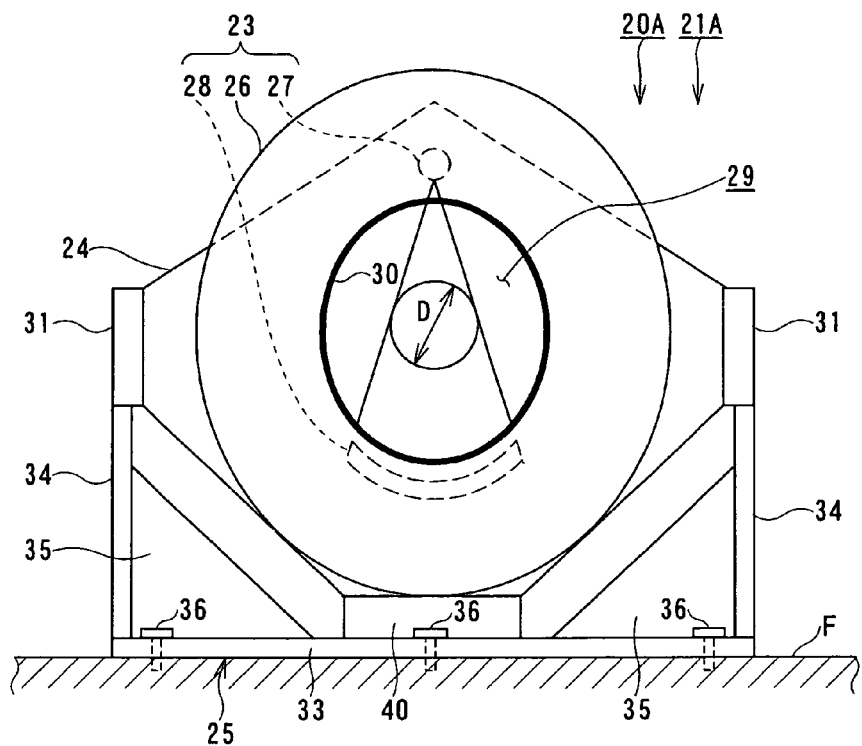
FIG. 4 is a front view showing an X-ray CT apparatus according to a second embodiment of the present invention.
Figure 5:
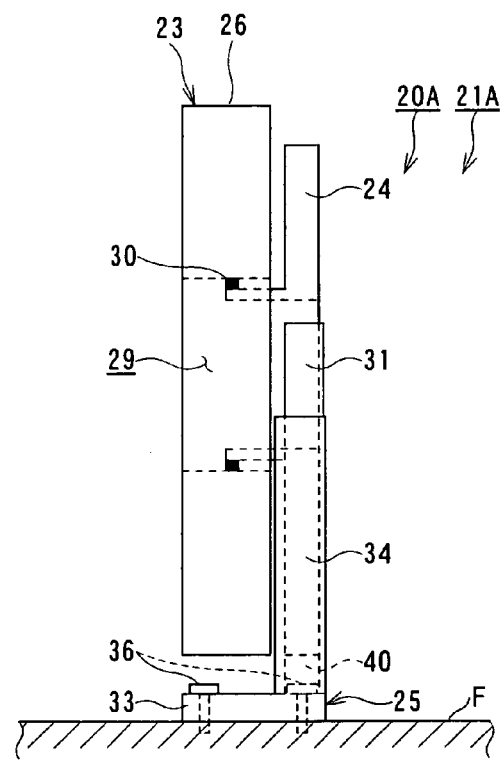
FIG. 5 is a side view of the gantry shown in FIG. 4.

FIG. 4 is a front view showing an X-ray CT apparatus according to a second embodiment of the present invention. FIG. 5 is a side view of the gantry 21 shown in FIG. 4.

In the X-ray CT apparatus 20A shown in FIG. 4, a structure having a spacer 40 between a mainframe 24 and a stand 25 is different from that of the X-ray CT apparatus 20 shown in FIG. 1. Other structures and operations of the X-ray CT apparatus 20A are not different from those of the X-ray CT apparatus 20 shown in FIG. 1 substantially. Therefore, the same numbers are attached to the same components as those of the X-ray CT apparatus 20 to omit explanation thereof.

In an X-ray CT apparatus 20A, the spacer 40 having a desired shape is provided between the mainframe 24 and the stand 25. That is, the lower section of the mainframe 24 is secured to the stand 25 via the spacer 40 either directly or indirectly.

Thus, the X-ray CT apparatus 20A can provide the same advantage as the X-ray CT apparatus 20 shown in FIG. 1.

Figure 6:
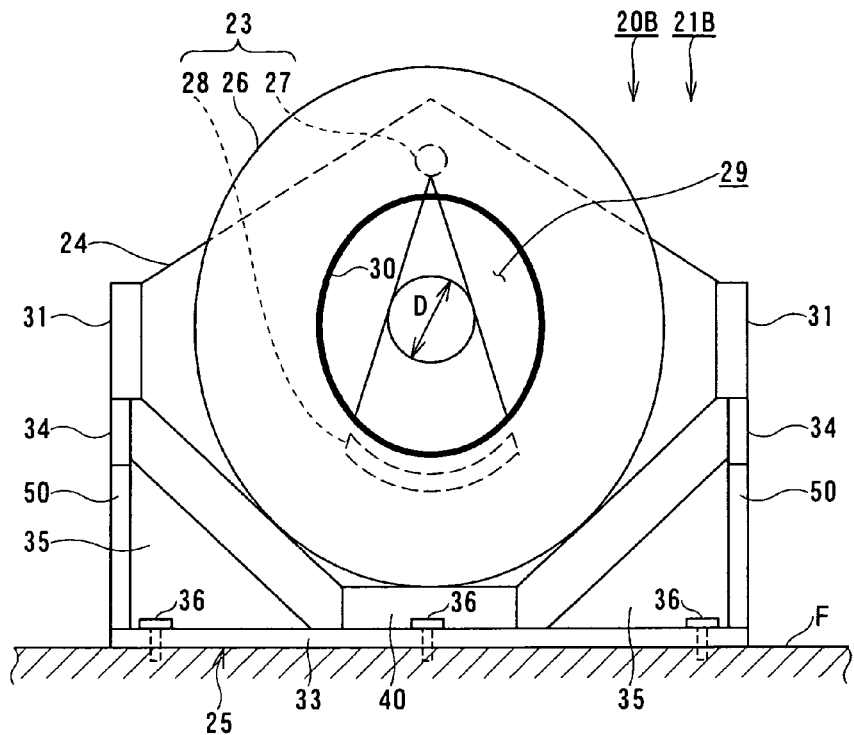
FIG. 6 is a front view showing a gantry of an X-ray CT apparatus according to a third embodiment of the present invention.
Figure 7:
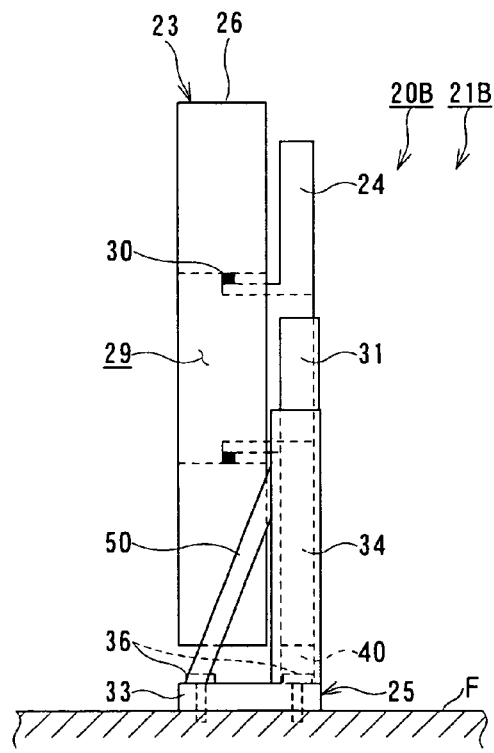
FIG. 7 is a side view of the gantry shown in FIG. 6.

Also, the X-ray CT apparatus 20A can facilitate the assembly thereof by reducing influence of variation in the shape and size of the parts. Furthermore, the spacer 40 can correct even a slight shift of the stand 25 from the mainframe 24 that occurred during the assembly. As a result, a more precise image can be obtained. FIG. 6 is a front view showing a gantry of an X-ray CT apparatus according to a third embodiment of the present invention. FIG. 7 is a side view of the gantry 21 shown in FIG. 6.

In the X-ray CT apparatus 20B shown in FIG. 6, a structure having reinforcing columns 50 between each of the supporters 34 of the stand 25 and the lower member 33 is different from that of the X-ray CT apparatus 20A shown in FIG. 4. Other structures and operations of the X-ray CT apparatus 20B are not different from those of the X-ray CT apparatus 20A shown in FIG. 4 substantially. Therefore, the same numbers are attached to the same components as those of the X-ray CT apparatus 20A to omit explanation thereof.

The stand 25 of the X-ray CT apparatus 20B has the reinforcing columns 50 each having a columnar shape, e.g., at two points. More specifically, each longitudinal direction of the reinforcing columns 50 is inclined to each longitudinal direction of the supporters 34 so that each of the reinforcing columns 50 is set between each of the supporters 34 and the lower member 33.

In the X-ray CT apparatus 20B, the stand 25 having the reinforcing columns 50 in an oblique direction to the longitudinal direction of the supporters 34 make it possible to steady the X-ray CT apparatus 20B even if the gravity point of the gantry 21 is on the rotating part 23 side due to the detector 28 having many rows of detecting elements.

Note that, the shapes, the number and the positions of the reinforcing columns 50 may be changed arbitrarily for steadying the X-ray CT apparatus 20B.

Figure 8:
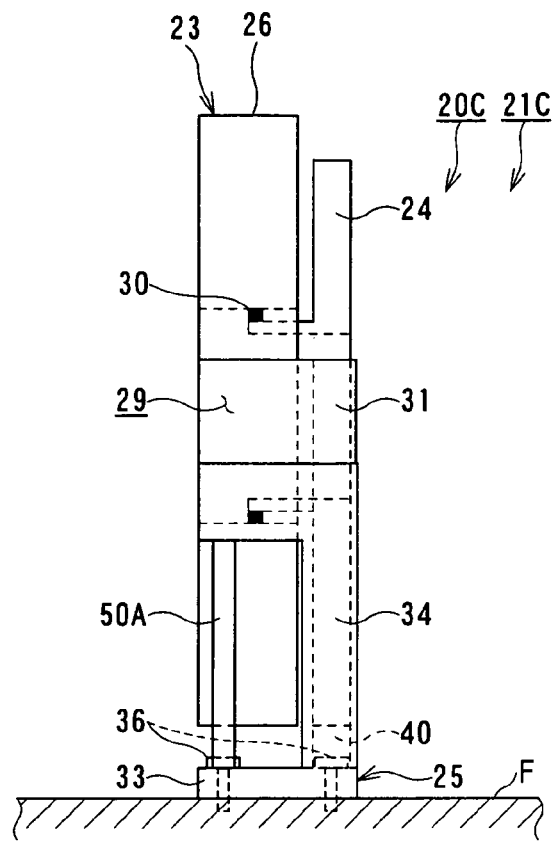
FIG. 8 is a side view of a modified example of the gantry shown in FIG. 6.
Figure 9:
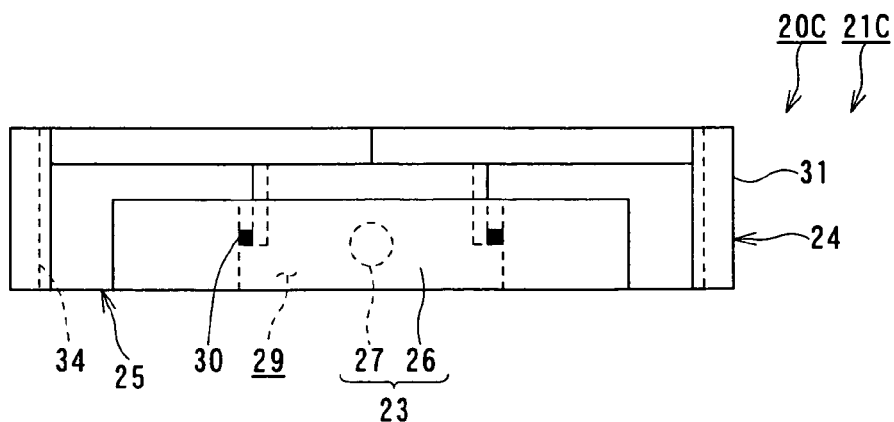
FIG. 9 is a top view of the gantry shown in FIG. 8.

FIG. 8 is a side view of a modified example of the gantry shown in FIG. 6. FIG. 9 is a top view of the gantry 21 shown in FIG. 8.

The stand 25 of the gantry 21 provided with an X-ray CT apparatus 20C shown in FIG. 8 includes supporters 34 each having a shape projecting toward the rotating part 23 side. Furthermore, each of the side supporting parts 31 of the mainframe 24 also has a shape projecting toward the rotating part 23 side. The supporters 34 support the side supporting parts 31 on larger range including the rotating part 23 side respectively. Each projecting rotating part 23 side of the supporters 34 is settled with the lower member 33 of the stand 25 by a corresponding columnar reinforcing column 50A.

Figure 10:
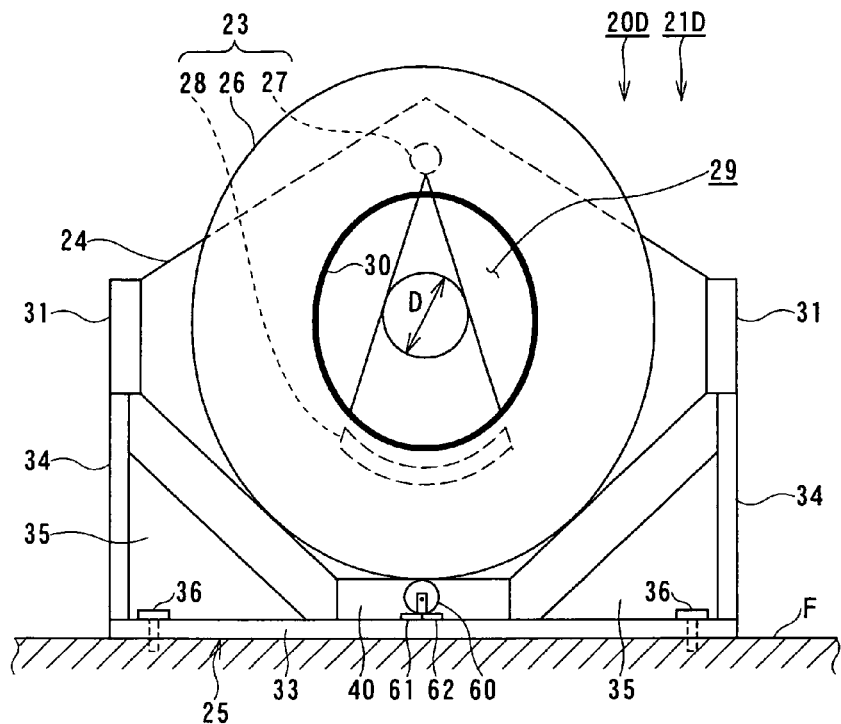
FIG. 10 is a front view showing a gantry of an X-ray CT apparatus according to a fourth embodiment of the present invention.
Figure 11:
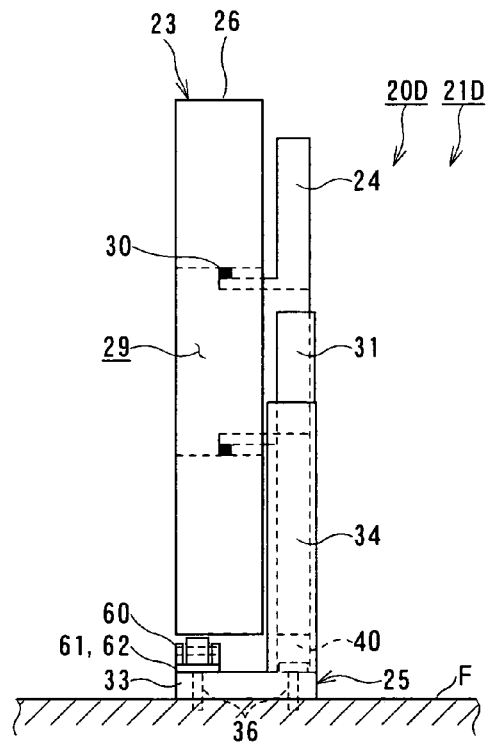
FIG. 11 is a side view of the gantry shown in FIG. 10.
Figure 14:
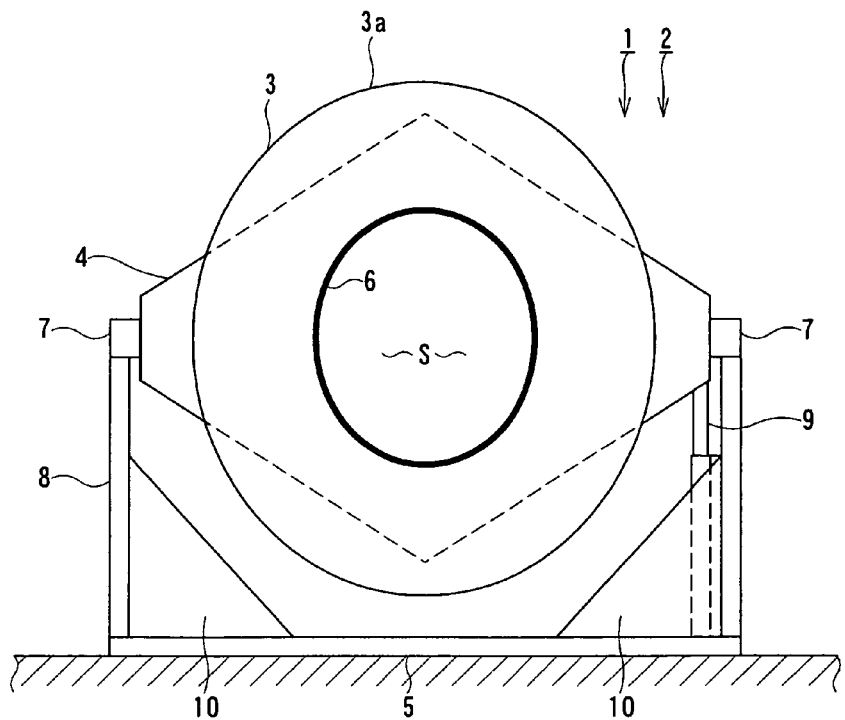
FIG. 14 is a front view showing a structure of a conventional X-ray CT apparatus.
Figure 15:
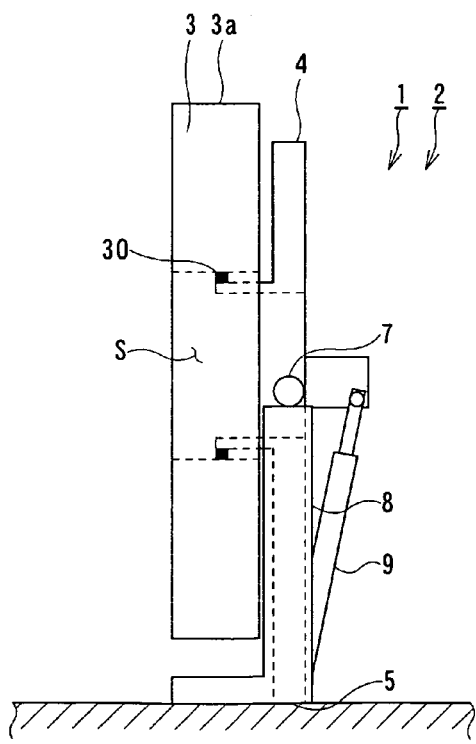
FIG. 15 is a side view of the conventional X-ray CT apparatus shown in FIG. 14.

In the X-ray CT apparatus 20C, since the supporters 34 projecting toward the rotating part 23 side are settled with the lower member 33 of the stand 25 by the reinforcing columns 50A respectively, the X-ray CT apparatus 20C is stabilized though the center of gravity of the gantry 21 is on the rotating part 23 side similarly to the case of the X-ray CT apparatus 20B shown in FIG. 6. FIG. 10 is a front view showing a gantry of an X-ray CT apparatus according to a fourth embodiment of the present invention. FIG. 11 is a side view of the gantry 21 shown in FIG. 10.

In the X-ray CT apparatus 20D shown in FIG. 10, structures having a roller 60 supporting the rotating part 23, a load cell 61 and a rotating meter 62 are different from those of the X-ray CT apparatus 20B shown in FIG. 6. Other structures and operations of the X-ray CT apparatus 20D are not different from those of the X-ray CT apparatus 20B shown in FIG. 6 substantially. Therefore, the same numbers are attached to the same components as those of the X-ray CT apparatus 20B to omit explanation thereof.

The X-ray CT apparatus 20D includes the roller 60 on the stand 25 near the rotating part 23. The rotating part 23 is partially supported by the rotating surface contacting therewith of the roller 60. The rotating axis of the roller 60 is to be parallel to that of the rotating part 23. Therefore, the rotatable rotating part 23 is supported by the roller 60 which can rotate in the direction opposite to a rotating direction of the rotating part 23.

In addition, the load cell 61 and the rotating meter 62 are provided with the roller 60. The load cell 61 has a function to measure a load applied to the roller 60. The rotating meter 62 has a function to measure a rotating speed of the roller 60.

According to the X-ray CT apparatus 20D described above, the effect similar to that in the X-ray CT apparatus 20B shown in FIG. 6 can be acquired. That is, supporting the rotating part 23 by the roller 60 steadies the gantry 21 of the X-ray CT apparatus 20D even if the weight of the rotating part 23 increases due to the detector 28 having many rows. Note that, not only the roller 60 but also a rotating structure such as a bearing can support the rotating part 23.

In addition, measuring the load variation applied to the roller 60 from the rotating part 23 by the load cell 61 allows the extraordinariness on the balance of the rotating part 23 to be detected. On the other hand, since measuring a rotating speed of the roller 60 by the rotating meter 62 allows the rotating speed of the rotating part 23 to be detected indirectly, variation and extraordinariness on the rotating speed of the rotating part 23 can be detected.

FIG. 12 is a front view showing a gantry of an X-ray CT apparatus according to a fifth embodiment of the present invention. FIG. 13 is a sectional view on A-A of the gantry 21 shown in FIG. 12;

In the X-ray CT apparatus 20E shown in FIG. 12, shapes of mainframe 24A and spacer 40A and a method for supporting the rotating part 23 are different from that of the X-ray CT apparatus 20B shown in FIG. 6. Other structures and operations of the X-ray CT apparatus 20E are not different from those of the X-ray CT apparatus 20B shown in FIG. 6 substantially. Therefore, the same numbers are attached to the same components as those of the X-ray CT apparatus 20B to omit explanation thereof.

In the gantry 21 of the X-ray CT apparatus 20E, the mainframe 24A is supported at three points of the two supporters 34 and the spacer 40A to be fixed with the stand 25. Furthermore, the mainframe 24A has a shape which forms dents nearer the rotation center side of the rotating part 23 than lines connecting the adjacent supporting points. In other words, the mainframe 24A has dents 70 in the center side of the rotating part 23 so as to form a shape of which the center side of the rotating part 23 is larger than each supporting point side.

Each of the dents 70 of the mainframe 24A expands each space between the mainframe 24A and the stand 25 or the electric components 35 to get a maintenance space for maintenance of components 71 provided with the rotating part 23 to generate or detect an X-ray. That is, maintenance spaces are formed between the adjacent supporting points of the mainframe 24A.

In particular, a device 71 attached to the high-voltage generator for supplying voltage with the X-ray tube 27 or a DAS (data acquisition system) for acquiring X-ray detection data from the detector 28 is often arranged in the mainframe 24A side of the rotational base 26. It is preferable to conduct maintenance for the device 71 as described above from the mainframe 24A side. In order to respond such a situation, the gantry 21 of the X-ray CT apparatus 20E forms maintenance spaces for conducting maintenance from the mainframe 24A side.

Therefore, the gantry 21 of the X-ray CT apparatus 20E achieves easily conducting maintenance of components 71. The Larger dent 70 of the mainframe 24A allows a larger maintenance space to be acquired. On the other hand, it is necessary to settle the mainframe 24A with the stand 25 with sufficient strength.

So conditions for getting a larger maintenance space with sufficiently tight-settling the mainframe 24A with the stand 25 are considered.

As shown in FIG. 12, "a" denotes the width of the spacer 40A and "b" denotes the width of the stand 25. Further, "c" denotes the length of each of the side supporting parts 31 of the mainframe 24A in the vertical direction and "h" denotes the height obtained by adding the length c of the side supporting parts 31 in the vertical direction to the height of the stand 25 in the vertical direction.

In the case, on supporting both side of the mainframe 24A, it is considered that the value of c/h of ½ and above gives a useful and sufficient strength empirically for obtaining satisfactory image quality. In particular, it is considered that vibration of the rotating part 23 is suppressed sufficiently to get a spatial resolution necessary for visibility of an object having a size of 0.5 mm. As a similar viewpoint, on supporting lower part of the mainframe 24A, it is considered that the value a/b between ½ and ¼ is sufficient.

On the other hand, the spacer 40A may have a shape which projects from the mainframe 24A in the rotating direction of the rotating part 23 as shown in FIG. 13. As described above, the spacer 40A having a shape of trapezoid pole allows the width a of the spacer 40A to be reduced to get a maintenance space with a sufficient strength even if the rotating part 23 is heavy.

In addition, supporting the rotating part 23 by bearings 30 at a plurality of portion also improves image quality with suppressing vibration of the rotating part 23. FIG. 13 shows an example of the rotating part 23 supported at two portions by the mainframe 24A through the bearings 30. Not only an example shown in FIG. 13, but a method in which the rotating part 23 is supported at it's both side by a plurality of mainframes can be employed.

Note that, arbitrary components of the above-mentioned X-ray CT apparatuses 20, 20A, 20B, 20C, 20D and 20E according to embodiments may be combined into a single X-ray CT apparatuses. On the contrary, partially components of the X-ray CT apparatuses 20, 20A, 20B, 20C, 20D and 20E may be omitted as long as necessary functions are got.

What is claimed is:

1. An X-ray CT apparatus, comprising:
    a rotating part configured to mount an X-ray tube and a detector including detecting elements arranged in a plurality of rows and each of the detecting elements having a width of 0.5 mm or less, wherein the rotating part is configured to rotate at a speed faster than 0.5 second/rotation by an operation of a rotary drive structure, and the rotating part has a non-tilt structure;
    a fixed frame as a single plate-like member configured to support the rotating part and prevent the rotating part from tilting, the fixed frame including a lower supporting part; and
    a stand configured to support the fixed frame and configured to be settled to a floor,
    wherein the stand includes:
        a lower member configured to be settled to the floor, and the lower member is directly connected to the lower supporting part of the fixed frame;

supporters each configured to support each side of the fixed frame and configured to be settled to the lower member; and
a fixing member configured to fix a lower part of the fixed frame to the lower member;
a roller positioned on the stand; and
a load cell configured to measure a load variation applied to the roller via by the rotating part.

2. An X-ray CT apparatus according to claim 1, wherein the lower member is configured to be settled to the floor near the supporters and the fixed frame by anchor bolts respectively.

3. An X-ray CT apparatus according to claim 1, wherein the fixed frame is supported by at least three points with the stand.

4. An X-ray CT apparatus according to claim 1, wherein the rotating part has a space having an opening configured to receive an object, the opening having a diameter of 90 cm above.

5. An X-ray CT apparatus according to claim 1, wherein the stand includes a reinforcing member between at least one of the supporters and the lower member.

6. An X-ray CT apparatus according to claim 1, further comprising a rotating structure on the stand to support a part of the rotating part, the fixed frame being configured to support the rotating part on contact with the rotary drive structure.

7. An X-ray CT apparatus according to claim 1, wherein the fixing member has a shape projecting from the fixed frame to a rotating part side.

8. An X-ray CT apparatus according to claim 1, wherein the fixed frame is configured to support the rotating part by at least two positions.

9. An X-ray CT apparatus, comprising:
a rotating part configured to mount an X-ray tube and a detector including detecting elements arranged in a plurality of rows and each of the detecting elements having a width of 0.5 mm or less, wherein the rotating part is configured to rotate at a speed faster than 0.5 second/rotation by an operation of a rotary drive structure, and the rotating part has a non-tilt structure;
a mainframe as a single plate-like member configured to support the rotating part and prevent the rotating part from tilting, the mainframe including a lower supporting part;
a lower member of a stand directly connected to the lower part of the mainframe and configured to be settled to a floor; and
supporters each configured to support each side of the mainframe, the supporters configured to be settled to the lower member;
a roller positioned on the stand; and
a load cell configured to measure a load variation applied to the roller via by the rotating part.

10. An X-ray CT apparatus, comprising:
a rotating part configured to mount a device configured to generate an X-ray and a device configured to detect the X-ray, the device configured to detect the X-ray including detecting elements arranged in a plurality of rows and each of the detecting elements having a width of 0.5 mm or less, wherein the rotating part is configured to rotate at a speed faster than 0.5 second/rotation by an operation of a rotary drive structure and the rotating part has a non-tilt structure;
a fixed frame as a single plate-like member configured to support the rotating part on contact with the rotary drive structure and prevent the rotating part from tilting, the fixed frame including a lower supporting part; and
a stand configured to support the fixed frame by at least three supporting points, the stand including a lower member configured to be settled to the floor, and the lower member is directly connected to the lower supporting part of the fixed frame,
wherein the fixed frame and the stand are configured to form a space for a maintenance of at least one of the device configured to generate the X-ray and the device configured to detect the X-ray between one of the three supporting points and another;
a roller positioned on the stand; and
a load cell configured to measure a load variation applied to the roller via by the rotating part.

11. An X-ray CT apparatus according to claim 10, wherein the fixed frame has a shape in which a size of the space for the maintenance near a rotation center side of the rotating part is larger than that near a line connected adjacent supporting points.

12. An X-ray CT apparatus according to claim 10, wherein the fixed frame has a dent near a rotation center side of the rotating part.

13. An X-ray CT apparatus according to claim 10, wherein the fixed frame is configured to support a lower part of the rotating part at one of the three supporting points, a supporting part for the lower part having a width of ½ to ¼ of a width of the stand.

14. An X-ray CT apparatus according to claim 10, wherein the fixed frame is configured to support a side part of the rotating part at one of the three supporting points, a supporting part for the side part having a length longer than ½ of a height of the stand including a length of the supporting part.

15. An X-ray CT apparatus according to claim 10, wherein the stand is configured to support right and left sides and a lower part of the fixed frame.

* * * * *